(12) United States Patent
Gudmundsson et al.

(10) Patent No.: US 12,031,968 B2
(45) Date of Patent: Jul. 9, 2024

(54) DISTRIBUTION UNIT FOR MILK SAMPLES COMPRISING TWO SEPARATE PARTS

(71) Applicant: DELAVAL HOLDING AB, Tumba (SE)

(72) Inventors: Mats Gudmundsson, Tumba (SE); Thomas Johansson, Tumba (SE)

(73) Assignee: DeLaval Holding AB, Tumba (SE)

( * ) Notice: Subject to any disclaimer, the term of this patent is extended or adjusted under 35 U.S.C. 154(b) by 497 days.

(21) Appl. No.: 17/288,474

(22) PCT Filed: Oct. 21, 2019

(86) PCT No.: PCT/SE2019/051033
§ 371 (c)(1),
(2) Date: Apr. 23, 2021

(87) PCT Pub. No.: WO2020/085980
PCT Pub. Date: Apr. 30, 2020

(65) Prior Publication Data
US 2021/0389291 A1    Dec. 16, 2021

(30) Foreign Application Priority Data

Oct. 25, 2018 (SE) .................................. 1800204-8

(51) Int. Cl.
*G01N 33/04* (2006.01)
*A01J 5/04* (2006.01)

(52) U.S. Cl.
CPC ............. *G01N 33/04* (2013.01); *A01J 5/045* (2013.01)

(58) Field of Classification Search
CPC ......... G01N 33/04; A01J 5/045; A01J 5/0131; A01J 5/0132
See application file for complete search history.

(56) References Cited

U.S. PATENT DOCUMENTS

| 4,900,683 A | * | 2/1990 | Metzger | ................... G01N 1/28 436/179 |
| 2005/0217351 A1 | * | 10/2005 | Kreck | ...................... G01N 1/26 73/863.02 |

(Continued)

FOREIGN PATENT DOCUMENTS

| WO | 2012/087235 | 6/2012 |
| WO | 2013/032397 | 3/2013 |
| WO | 2017/030495 | 2/2017 |

OTHER PUBLICATIONS

International Search Report for PCT/SE2019/051033 dated Jan. 2, 2020, 4 pages.

(Continued)

*Primary Examiner* — Helen C Kwok
(74) *Attorney, Agent, or Firm* — NIXON & VANDERHYE (57) ABSTRACT

A distribution unit for milk samples that includes a first distribution portion with a first flow channel and a plurality of ports adjoining and communicating with the first flow channel, the ports configured to permit various media to be delivered to and from the first flow channel, and a second distribution portion that includes a second flow channel and a plurality of ports adjoining and communicating with the second flow channel, including at least a milk inlet port permitting milk to be delivered from the first flow channel to the second flow channel, and including a milk outlet port permitting milk samples to be delivered from the second flow channel to a further milk analyzing unit.

11 Claims, 7 Drawing Sheets

(56) References Cited

U.S. PATENT DOCUMENTS

| | | | |
|---|---|---|---|
| 2006/0283269 A1* | 12/2006 | Anderson | A01J 5/045 73/863.02 |
| 2009/0173281 A1* | 7/2009 | Bosma | A01J 5/045 119/14.08 |
| 2011/0132264 A1* | 6/2011 | Akerman | A01J 5/0135 119/14.08 |
| 2013/0247692 A1* | 9/2013 | Gudmundsson | A01J 5/045 73/863.02 |
| 2018/0235171 A1* | 8/2018 | Helgén | G01N 33/04 |

OTHER PUBLICATIONS

Written Opinion of the ISA for PCT/SE2019/051033 dated Jan. 2, 2020, 6 pages.
Swedish Search Report for SE 1800204-8 dated Oct. 25, 2018, 2 pages.

\* cited by examiner

DISTRIBUTION UNIT FOR MILK SAMPLES COMPRISING TWO SEPARATE PARTS

CROSS-REFERENCE TO RELATED APPLICATIONS

This application is the U.S. national phase of International Application No. PCT/SE2019/051033 filed Oct. 21, 2019 which designated the U.S. and claims priority to SE 1800204-8 filed Oct. 25, 2018, the entire contents of each of which are hereby incorporated by reference.

TECHNICAL FIELD OF THE INVENTION

The present invention refers to a distribution unit for milk samples.

BACKGROUND AND PRIOR ART

During a milking operation, the milk obtained from an animal is typically transferred to a local milk receiver. When the milking operation has been finished, a milk pump feeds the milk from the local milk receiver to a milk tank configured to receive milk from several local milk receivers. From the milk tank, the milk may then be delivered to the dairy industry for further processing. Before or during feeding of the milk to the milk tank, milk samples of individual animals may be taken. The milk samples may be subjected to various analyzes of traditional milk parameters reflecting the quality of the milk, such as the content of fat, protein and lactose.

The milk to be analyzed may be distributed to different analyzing units via a distribution unit. WO 2017/030495 discloses an example of such a distribution unit for milk samples, which comprises a flow passage, a valve controlled milk inlet port through which milk is delivered to the flow passage, a pump port through which a sampling pump communicates with the flow passage, and at least two valve controlled milk sampling outlet ports through which milk samples are delivered from the flow passage to a respective milk sample analyzing unit. The flow passage has a longitudinal extension between a first end and a second end. The milk sampling outlet ports are connected to the flow passage in positions located between the connection position of the milk inlet port and the connection position of the pump port.

A more advanced milk analyzing unit, configured for analyzing more advanced milk parameters such a progesterone, LDH—Lactate Dehydrogenase, Urea, BHB—Beta Hydroxy Butyrate, etc., may be connected to the distribution unit. The analysis of these parameters is more time consuming than the analysis of the traditional milk parameters such as fat, protein and lactose contents. Consequently, when a milk sample is delivered to the more advanced milk analyzing unit, a situation may occur that the more advanced analyzing unit is busy, and that the milk sample cannot be received and analyzed by the further analyzing unit. Thus the distribution units known from the prior art cannot secure an advanced analysis of all milk samples.

SUMMARY OF THE INVENTION

The purpose of the present invention is to remedy the problem discussed above, and provide a distribution unit which enables an efficient analysis of advanced parameters of the milk without negatively affecting the analysis of the traditional milk parameters.

This purpose is achieved by the distribution unit initially defined, which is characterized in that it comprises a second distribution portion comprising a flow channel and a plurality of ports, which adjoin and communicate with the flow channel of the second distribution portion, and comprise at least a milk inlet port, permitting milk to be delivered from the flow channel of the first distribution portion to the flow channel of the second distribution portion, and a milk outlet port, permitting milk samples to be delivered from the flow channel of the second distribution portion to a further milk analyzing unit.

By providing the second distribution portion, milk samples to be subjected to a more advanced and time consuming analysis may be transferred from the flow channel of the first distribution portion to the flow channel of the second distribution portion, where these milk samples may be stored and treated consecutively without affecting the work flow for analyzing the milk samples from the first distribution portion.

According to an embodiment of the invention, each of the milk samples to be delivered to the further milk analyzing unit has a determined volume being sufficient for permitting the further milk analyzing unit to perform a milk analysis, wherein the second distribution portion provides a milk storing volume that is greater than said determined volume. In such a way, it is possible to store at least one milk sample in the second distribution portion at the same time as the preceding milk sample is analyzed in the further milk analyzing unit.

According to an embodiment of the invention, the second distribution portion provides a milk storing volume that is at least twice said determined volume. Thus, it may be possible to store at least two milk samples waiting for being analyzed by the further milk analyzing unit. Advantageously, the second distribution portion may provide a milk storing volume that is at least three times greater than said determined volume, at least four times greater than said determined volume or at least five times greater than said determined volume.

According to an embodiment of the invention, the second distribution portion comprises an outlet conduit connecting the milk outlet port to the further milk analyzing unit, wherein the outlet conduit provides the milk storing volume and thus has an internal volume that is greater than said determined volume.

According to an embodiment of the invention, the further milk analyzing unit is located at a remote position at a distance from the distribution unit, and from the second distribution portion. The further milk analyzing unit may for instance be located at a central control space common for a plurality of milk stations. The first distribution portion and the second distribution portion as well as a milk receiver may be located at local position at or in a milking station.

According to an embodiment of the invention, said distance may be at least 5 m, at least 10 m or at least 15 m.

According to an embodiment of the invention, the ports of the second distribution portion also comprises a liquid inlet port, connected to a liquid source via a liquid inlet valve, and a gas inlet port, connected to a gas source via a gas inlet valve.

According to an embodiment of the invention, the distribution unit comprises a control unit configured to permit liquid to be delivered from the liquid source to the flow channel of the second distribution portion by opening the liquid inlet valve.

According to an embodiment of the invention, the control unit is configured to open the liquid inlet valve after said determined volume of milk has been delivered from the flow channel of the first distribution portion to permit a volume of liquid to be introduced into the flow channel of the second distribution portion and to be located behind the said determined volume of milk in the flow direction. The volume of liquid may thus create a limit of said determined volume of milk to permit said determined volume of milk to be separated from the following milk sample.

According to an embodiment of the invention, the control unit is configured to permit pressurized gas to be delivered from the gas source to the flow channel of the second distribution portion by opening the gas inlet valve.

According to an embodiment of the invention, the control unit is configured to open the gas inlet valve after said volume of liquid has been delivered from the liquid source to permit pressurized gas to be introduced into the flow channel of the second distribution portion in order to push said volume of liquid and said determined volume of milk in the flow direction towards the further milk analyzing unit. The pressurized gas from the gas source may thus provide the transport of the milk samples separated from each other from the flow channel of the second distribution portion to the further milk analyzing unit via the outlet conduit.

According to an embodiment of the invention, the flow channel of the second distribution portion is separated from the flow channel of the first distribution portion.

According to an embodiment of the invention, the first distribution portion comprises an upper part through, which the ports of the first distribution portion extend, and the second distribution portion comprises an upper part, through which the ports of the second distribution portion extend, wherein the upper part of the first distribution portion is separated from the upper part of the second distribution portion.

According to an embodiment of the invention, the flow channel of the first distribution portion and the flow channel of the second distribution portion extend in parallel with a common longitudinal axis.

DETAILED DESCRIPTION OF EMBODIMENTS OF THE INVENTION

Figure 1:
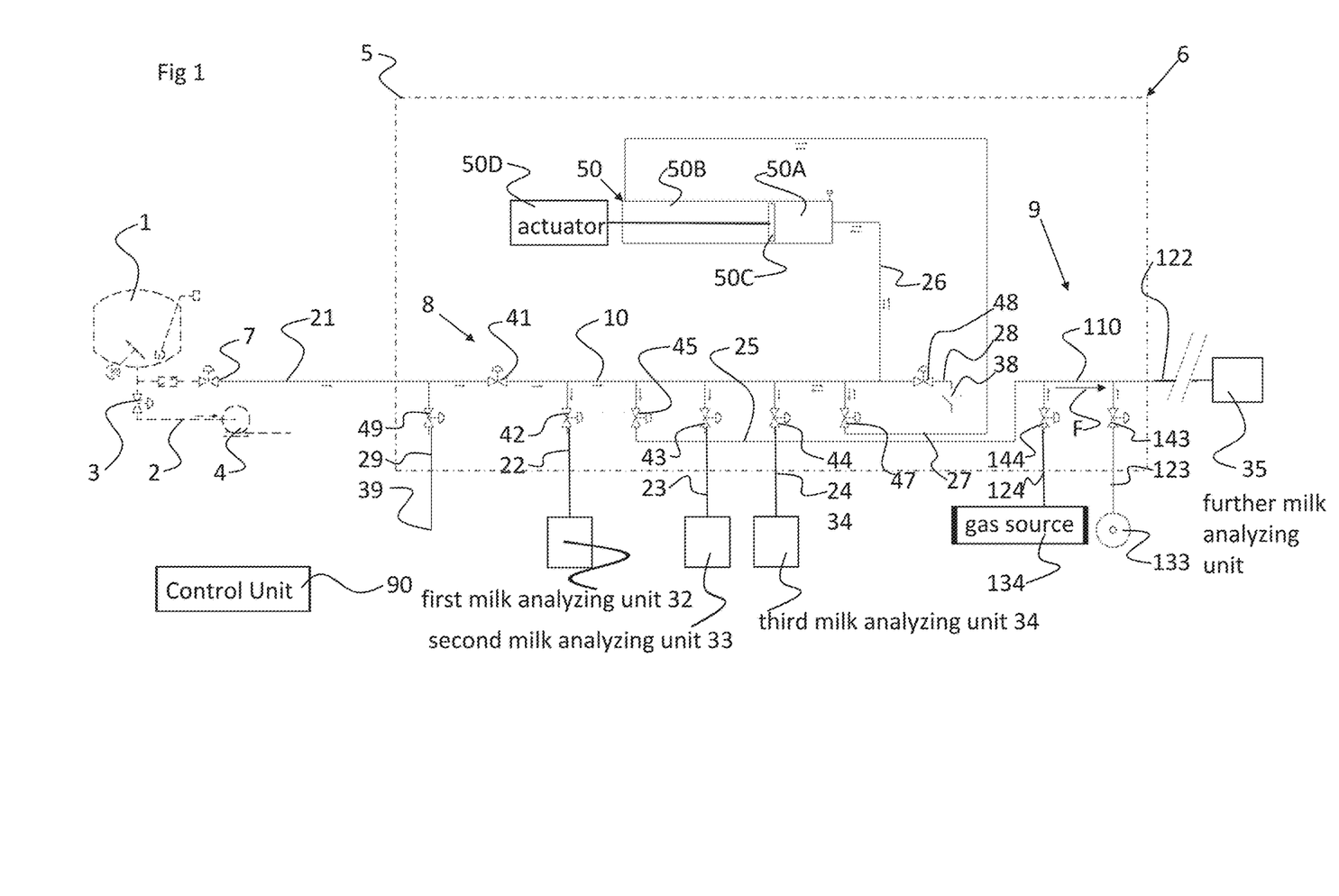
FIG. 1 shows schematically a milk sampling device including a distribution unit according to the invention.

FIG. 1 discloses a milk receiver 1 collecting milk from animals milked by milking machine. The milk receiver 1 may be located at a local position at or in a milking station, in which the animal is milked, for instance a voluntary robotic milking station.

A milk line 2 is connected to a bottom portion of the milk receiver 1. The milk line 2 comprises a valve 3 and a milk pump 4. When the valve 3 is in an open position and the milk pump 4 is activated, milk is pumped from the milk receiver 1, via the milk line 2, to a milk tank (not disclosed) that may be arranged to collect milk from several milk receivers 1.

FIG. 1 also discloses a milk sampling device 5 configured to receive milk samples of the milk from the milk receiver 1 before the milk is transported to the milk tank. The milk sampling device 5 comprises a distribution unit 6, which is disclosed more in detail in FIGS. 2-14. A main valve 7 is provided for opening and closing the transport of milk from the milk receiver 1 to the milk sampling device 5. Also, the distribution unit 6 may be located at a local position at or in the milking station.

Figure 2:
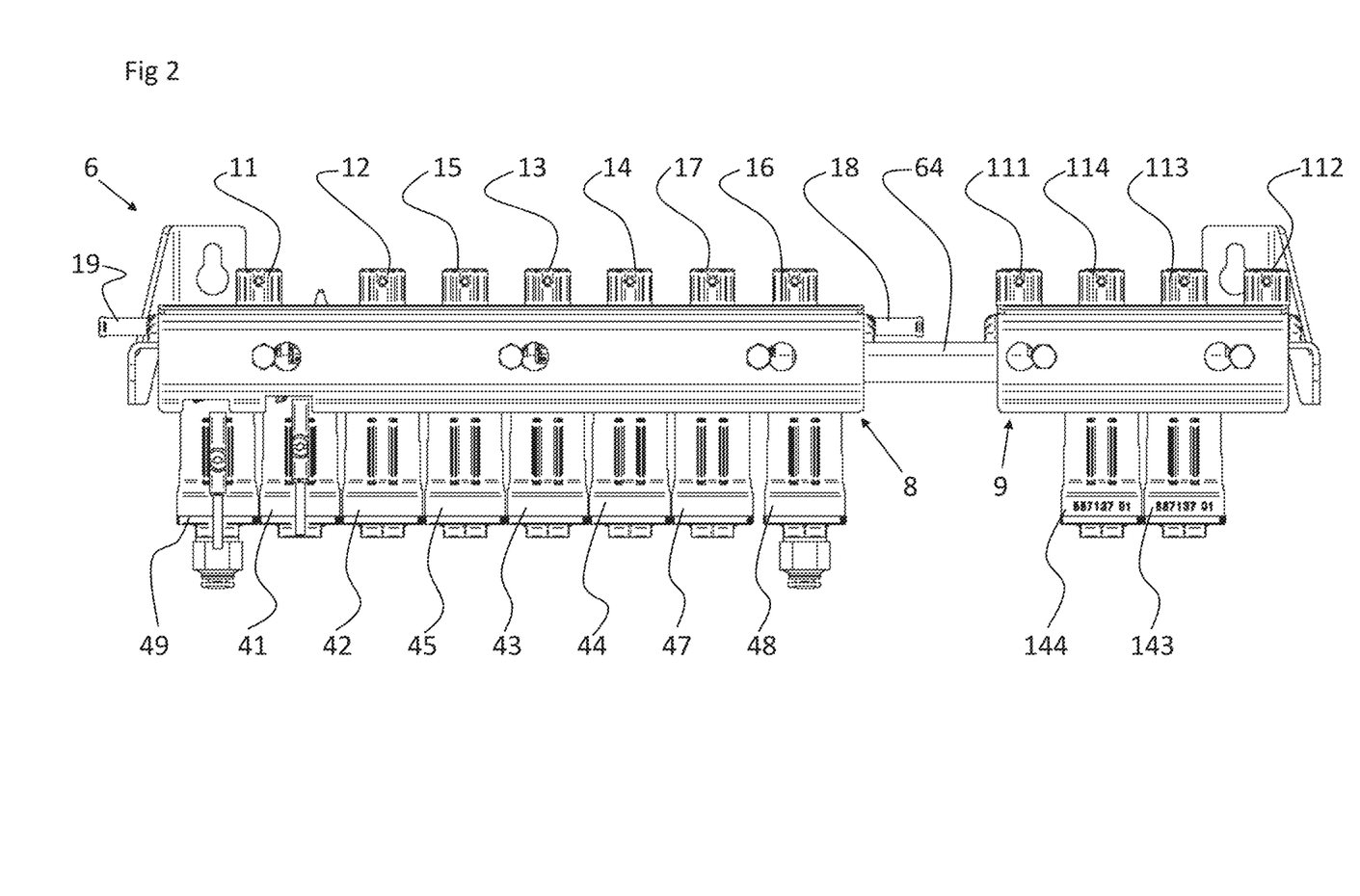
FIG. 2 shows a side view of the distribution unit.
Figure 3:
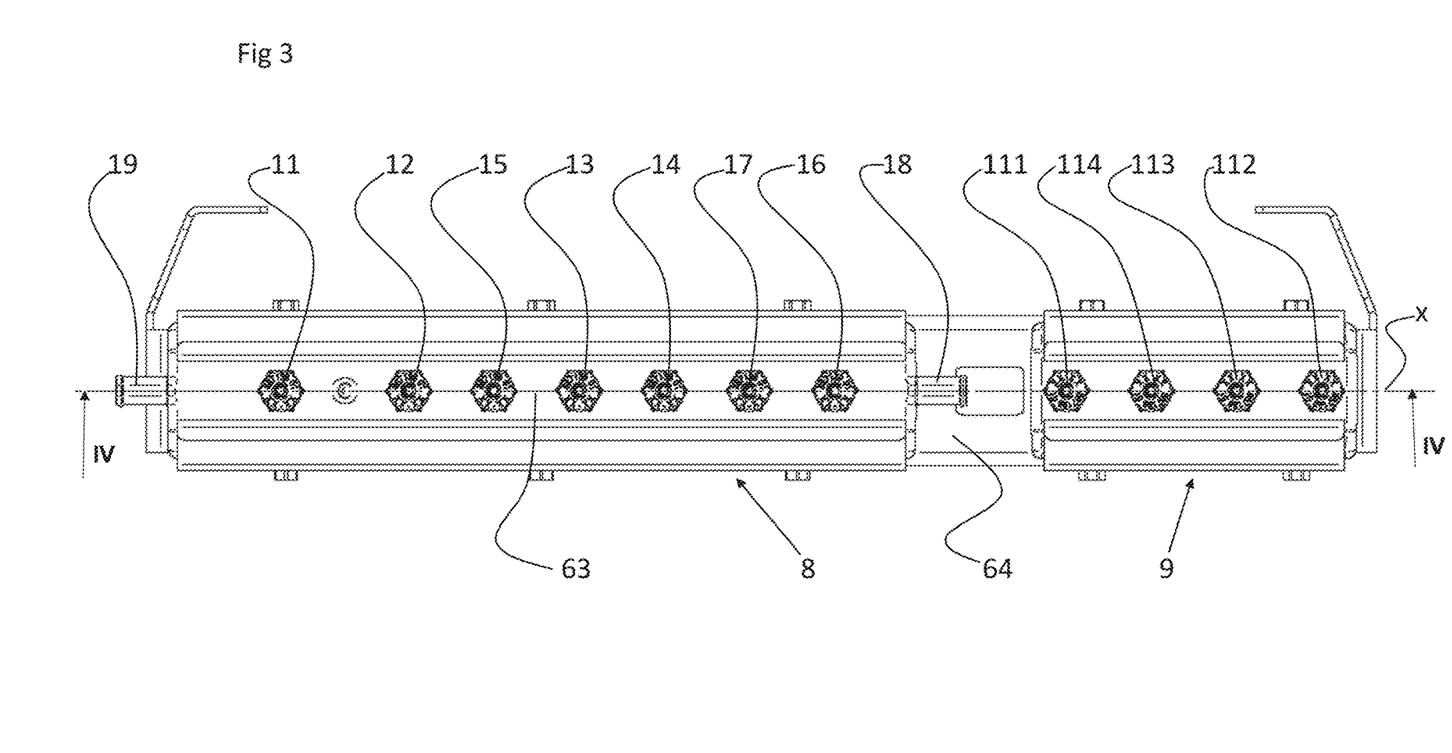
FIG. 3 shows view from above of the distribution unit.
Figure 4:
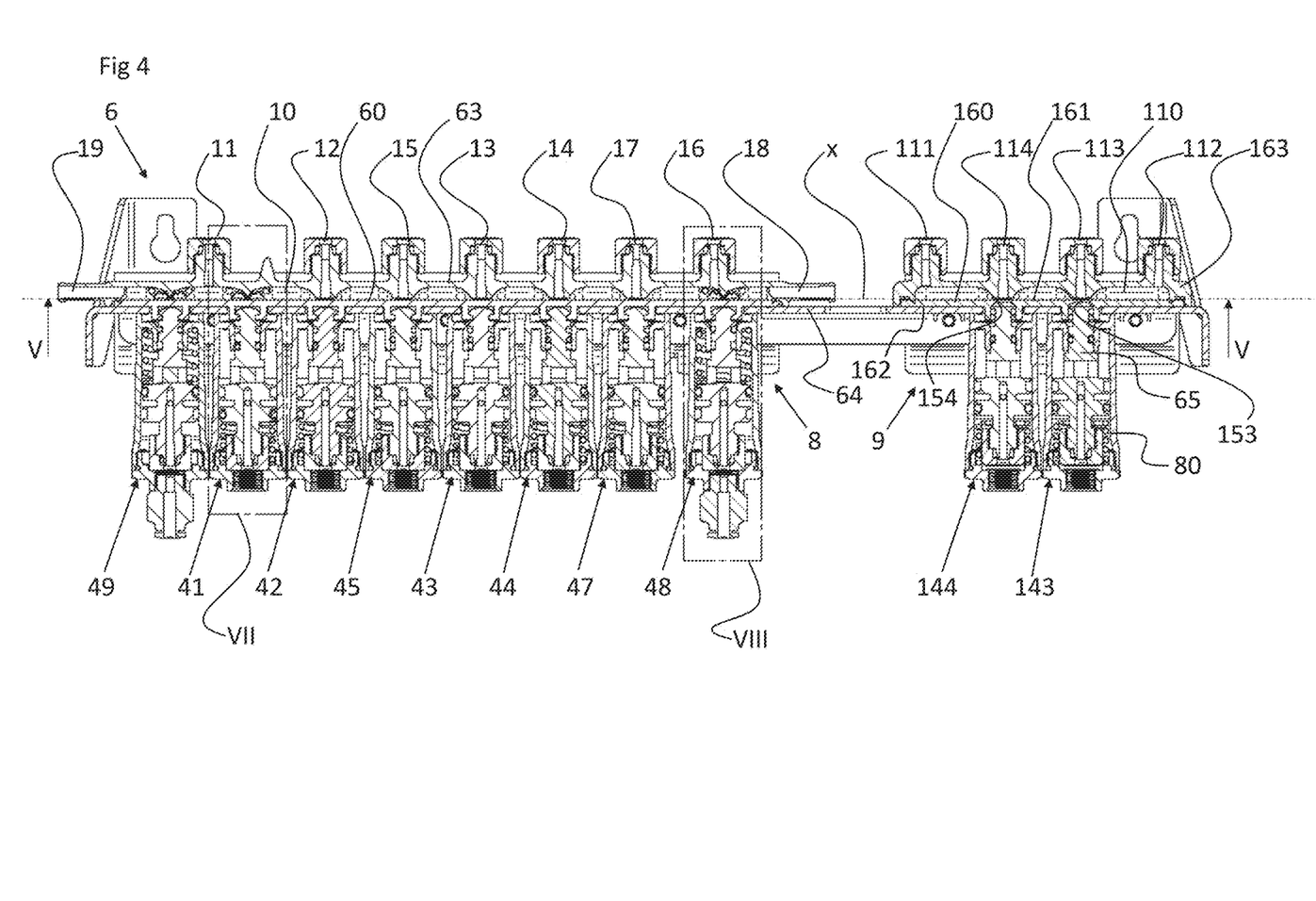
FIG. 4 shows a sectional view along the line IV-IV in FIG. 3.

As can be seen in FIGS. 2-4, the distribution unit 6 comprises a first distribution portion 8 and a second distribution portion 9.

The First Distribution Portion

The first distribution portion 8 comprises a flow channel 10 and a plurality of ports 11-19, which communicate with the flow channel 10. As can be seen in FIG. 4, the flow channel 10 has an elongated shape and extends along a longitudinal axis x.

The ports 11-19 are configured to permit various media, such as milk, washing liquid, water, gas and/or pressurized air, to be delivered to and from the flow channel 10.

More specifically, the ports 11-19 comprise a milk inlet port 11, permitting milk to be delivered to the flow channel 10, four milk outlet ports 12-15, permitting milk samples to be delivered from the flow channel 10, a first pump port 16, a second pump port 17, a drain port 18 and a bleed port 19.

The number of milk outlet ports 12-15 may be less or more than four depending on the number of different tests to be made on the milk.

The milk inlet port 11 is connected to the milk receiver 1 via an inlet conduit 21. The main valve 7 is provided on the inlet conduit 21. By opening the main valve 7, milk is permitted to be delivered from the milk receiver 1 to the flow channel 10. An inlet valve 41 is provided to open and close the inlet port 11.

The milk outlet port 12 is via a first outlet conduit 22 connected to a first milk analyzing unit 32, and permits milk samples to be delivered from the flow channel 10 to the first milk analyzing unit 32. A first outlet valve 42 is provided to open and close the milk outlet port 12.

The milk outlet port 13 is via second outlet conduit 23 connected to a second milk analyzing unit 33, and permits milk samples to be delivered from the flow channel 10 to the second milk analyzing unit 33. A second outlet valve 43 is provided to open and close the milk outlet port 13.

The milk outlet port 14 is via third outlet conduit 24 connected to a third milk analyzing unit 34, and permits milk samples to be delivered from the flow channel 10 to the third milk analyzing unit 34. A third outlet valve 44 is provided to open and close the milk outlet port 14.

The milk outlet port 15 is via fourth outlet conduit 25 connected to a milk inlet port 111 of the second distribution portion 9, and permits milk samples to be delivered from the flow channel 10 of the first distribution portion 8 to the second distribution portion 9, and from the second distribution portion 9 to a further milk analyzing unit 35. A fourth outlet valve 45 is provided to open and close the milk outlet port 15.

The first pump port 16 is connected to a milk sampling pump 50 via a first pump conduit 26, and permits milk and/or washing liquid to be transported between a first chamber 50A of the milk sampling pump 50 and the flow channel 10, see FIG. 1.

The second pump port 17 is also connected to the milk sampling pump 50 via a second pump conduit 27, and permits milk and/or washing liquid to be transported between a second chamber 50B of the milk sampling pump 50 and the flow channel 10.

The milk sampling pump 50 comprises a piston 50C separating the first and second chambers 50A and 50B. The piston 50C is driven by an actuator 50D.

The drain port 18 is via a drain conduit 28 connected to a drain outlet 38. A drain valve 48 is provided to open and close the drain port 18.

The bleed port 19 is via a bleed conduit 29 connected to a bleed outlet 39. A bleed valve 49 is provided to open and close the bleed port 18.

The first pump port 16 thus communicates with the first chamber 50A to suck milk into the flow channel 10 from the milk receiver 1 to the flow channel 10, and to push milk from the flow channel 10 to the milk outlet ports 12-15 via the first pump conduit 26 and to the drain outlet 38 via the drain port 28.

The first distribution portion 8 comprises a membrane 60 having an elongated shape and extending in the flow channel 10 in parallel with the longitudinal axis x. The membrane 60 has a first side 61 facing the ports 11-29 and a second side 62 being opposite to the first side 61. The membrane 60 may be made of a rubber-like material.

Figure 5:
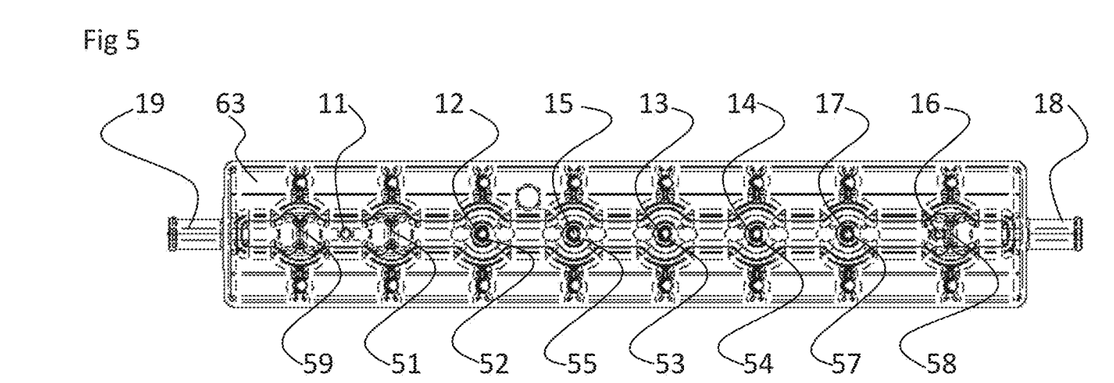
FIG. 5 shows a bottom view of an upper part of a first distribution portion of the distribution unit.
Figure 6:
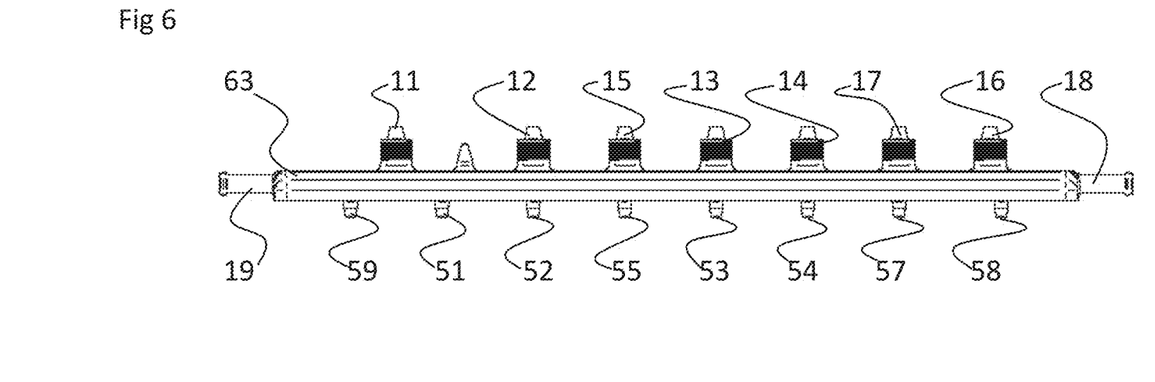
FIG. 6 shows a side view of the upper part.

The first distribution portion 8 comprises an upper part 63 and a lower part 64. The ports 11-29 extends through the upper part 63 as can be seen in FIGS. 4-6. The lower part 64 is configured as a console supporting the upper part 63 and the valves 41-49.

The first side 61 of the membrane 60 is smooth and turned towards the flow channel 10 and the upper part 63 of the first distribution portion 8. The flow channel 10 is thus defined by the upper part 63 and the first side 61 of the membrane 60.

Each of the ports 11-15 and 17-19 is associated with and provided adjacent to a seat surface 51-55 and 57-59. As can be seen in FIGS. 5 and 6, the pump port 16 is located close to, or adjacent, the seat surface 58, which is primarily associated with the drain port 18.

Each of the valves 41-49 comprises a valve body 65 acting on the second side 62 of the membrane 60 for closing and opening the ports 11-15 and 17-19.

Each of the valve bodies 65 is attached to the second side 62 of the membrane 60 to permit the valve body 65 to push the membrane 60 against the respective seat surface 51-55 and 57-59 for closing the respective port 11-15 and 17-19, and to pull the membrane 60 away from the respective seat surface 51-55 and 57-59 for opening the respective port 11-15 and 17-19.

As can be seen in FIGS. 9-13, the membrane 60 comprises a plurality of engagement elements 66 protruding from the second side 62 of the membrane 60. Each of the valve bodies 65 is attached to the second side 62 of the membrane 60 via a respective one of the engagement elements 66, see FIGS. 4, 7 and 8.

Figure 12:
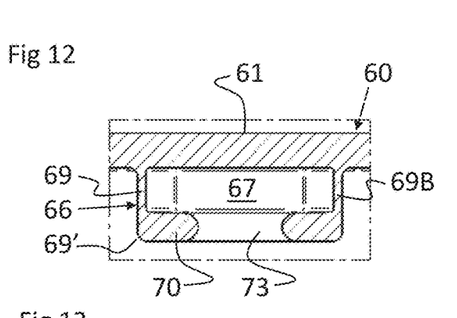
FIG. 12 shows sectional view along the line XII-XII in FIG. 10.
Figure 13:
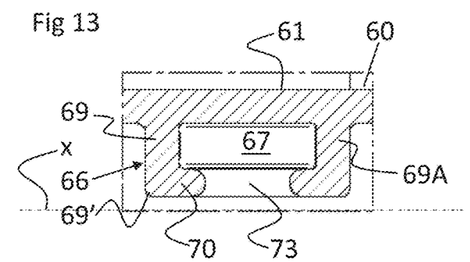
FIG. 13 shows an enlarged view of section XIII in FIG. 11.

Each of the engagement elements 66 comprises, or defines, a cavity 67, see FIGS. 12 and 13. Each of the valve bodies 65 comprises an end portion 68 forming an upper end of the valve body 65. Each of the end portions 68 is received in a respective one of the cavities 67. The end portion 68 may thus be gripped by the cavity 67, and may snap into the cavity 67.

Each of the engagement elements 66 comprises a wall member 69 extending from the second side 62 of the membrane 60 to an end of the wall member 69. The end of the wall member 69 is thus located at a distance from the second side 62 of the membrane 60. The wall member 69 surrounds at least partly the cavity 67.

Each of the engagement elements 66 comprises a projection 70 extending inwardly from the end of the wall member 69, and wherein the projection 70 projects into a depression 71 of the valve body 65, see FIGS. 7, 8, 12 and 13. The projection 70 forms a flange having an annular shape. The flange extends around and define an opening 73 to the cavity 67.

Each of the end portions 68 has an outer peripheral side surface 72. The depression 71 extends through the outer peripheral side surface 72. The depression 71 is annular and extends around the outer peripheral side surface 72 of the end portion 68 of the valve body 65. Thus the annular flange of the projection 70 of the engagement element 66 extends into and around the annular depression 71 of the end portion 68, when the membrane 60 is attached to the valve body 65, see FIGS. 7 and 8.

Figure 7:
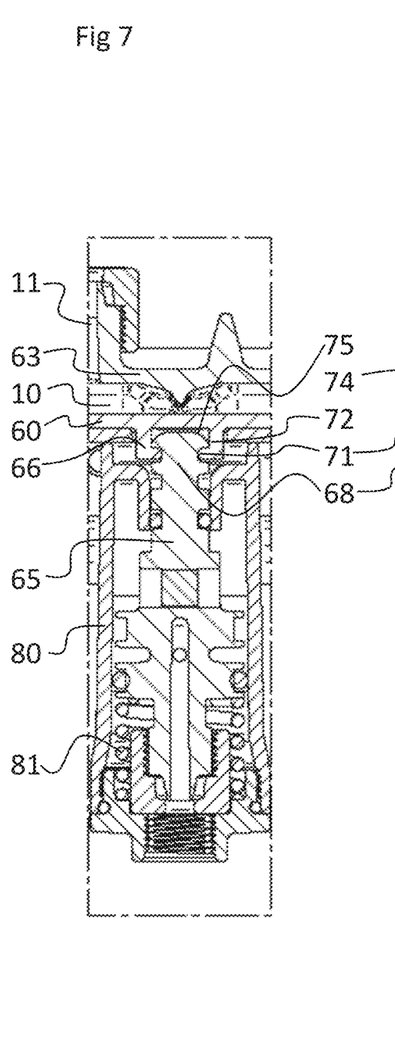
FIG. 7 shows an enlarged view of section V in FIG. 4.
Figure 8:
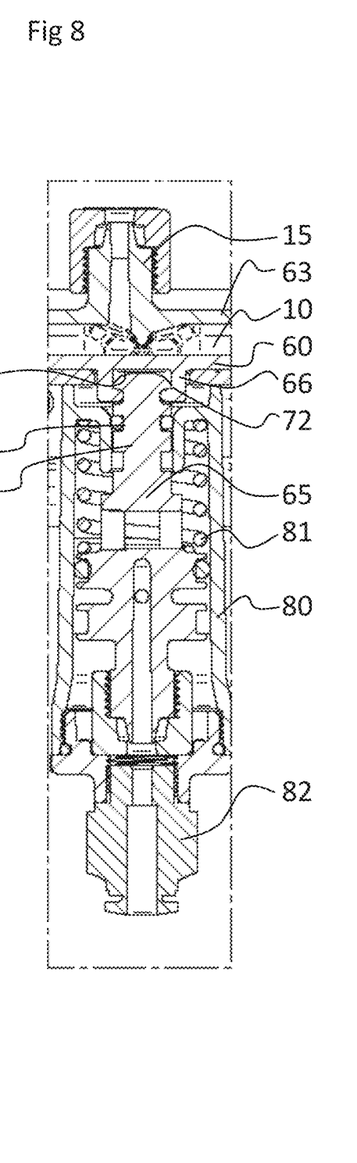
FIG. 8 shows an enlarged view of section VI in FIG. 4.
Figures 9, 10:
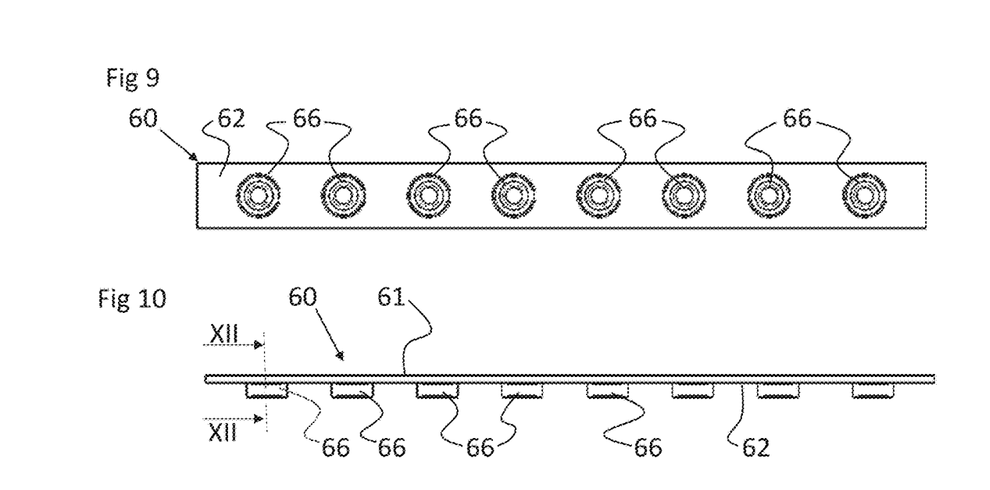
FIG. 9 shows bottom view of a membrane of the first distribution portion.
FIG. 10 shows side view of the membrane.
Figure 11:
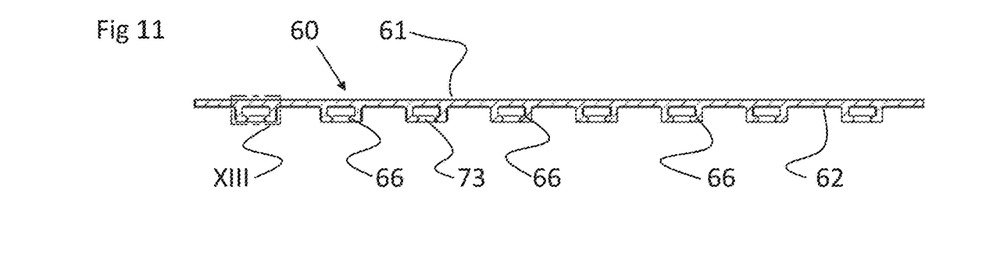
FIG. 11 shows sectional view along the line XI-XI in FIG. 10.

The cavity 67 has a substantially plane bottom surface 74, whereas the end portion 68 of the valve body 65 has a convexly domed end surface 75, which may abut the plane bottom surface 74 when the membrane 60 is attached to the valve body 65, see FIGS. 7 and 8. The convexly doomed end surface 75 and the plane bottom surface 74 provides an air cushion between the valve body 65 and the plane bottom surface 74.

The wall member 69 extends around and encloses the cavity 67 and has a varying wall thickness in a circumferential direction. In particular, the wall member 69 may comprise two first wall portions 69A which are located opposite to each other and are intersected by the longitudinal axis x, or a line being parallel to the longitudinal axis x, see FIG. 13, and two second wall portions 69B, which are located opposite to each other and provided between, and possibly, connecting the first wall portions 69A, see FIG. 12. The wall thickness of the first wall portions 69A are thicker than the wall thickness of the second wall portions 69B as can be seen in FIGS. 12 and 13.

As can be seen in FIG. 5, the seat surface 52-55, 57 of each of the milk outlet ports 12-15 and the second pump port 17 is annular and surrounds an opening of the respective milk outlet port 12-15 and second pump port 17. When the membrane 60 is pushed against one of the seat surface 52-55, 57, the first side 61 will abut the respective seat surface 52-55, 57 and enclose the opening of the respective port 12-15, 17, thereby closing the respective port 12-15, 17. The flow channel 10 will still permit passage of milk or washing liquid to pass beside the seat surface 52-55, 57 of the closed port 12-15, 17, to permit the milk or washing liquid to pass to and through another one of the ports 12-15, 17.

The seat surface 51, 58, 59 adjacent to and associated with milk inlet port 11, the drain port 18 and the bleed port 19, respectively, are provided beside the respective port 11, 18 and 19 and extends transversely to the flow channel 10. When the membrane 60 is pushed against one of the seat surface 51, 58, 59, the first side 61 will abut the respective seat surface 51, 58, 59 and close the opening of the respective port 11, 18, 19 from the flow channel 10.

Each of the valves 41-49 comprises a valve housing 80 in which the valve body 65 is provided. The valve body 65 is movable in the valve housing 80 in a first direction by supply of pressurized gas and in an opposite second direction by means of a compression spring 81, see FIGS. 7 and 8. The pressurized gas is supplied from a source (not disclosed) via an inlet nozzle 82, see FIG. 8.

In the valves 42-45, 47-49, the first direction is towards the respective seat surface 52-59. In the valve 41, the second direction is towards the seat surface 52.

The first, second and third milk analyzing units 32-34 may include means for analyzing for instance the following traditional milk parameters: fat content, protein content, lactose content, etc. As mentioned above, the invention is not restricted to the number of milk analyzing units disclosed but may be modified to include more milk analyzing units and thus also more milk outlet ports and valves from the first distribution portion 8 than those disclosed.

The milk sampling device 5 comprises a control unit 90 configured for controlling the operation of the milk sampling device 5 and the distribution unit 6, in particular for controlling the valves 7, 41-45, 47-49 and the actuator 50D of the milk sampling pump 50.

The Second Distribution Portion

The second distribution portion 9 comprises a flow channel 110 and a plurality of ports 111-114, which communicate with the flow channel 110.

As can be seen in FIG. 4, also the flow channel 110 has an elongated shape and extends along the longitudinal axis x. The flow channel 110 of the second distribution portion 9 is separated from the flow channel 10 of the first distribution portion 8.

The ports 111-114 are configured to permit various media, such as milk, washing liquid, water, gas and/or pressurized air, to be delivered to and from the flow channel 110.

More specifically, the ports 111-114 comprise a milk inlet port 111, a milk outlet port 112, a gas inlet port 113 and a liquid inlet port 114.

The milk inlet port 111 is connected to the milk outlet port 15 of the first distribution portion 8 via the fourth outlet conduit 25, and permits milk samples to be delivered from the flow channel 10 of the first distribution portion 8 to the flow channel 110 of the second distribution portion 9.

The milk outlet port 112 is via an outlet conduit 122 connected to the further milk analyzing unit 35 and permits milk samples to be delivered from the flow channel 110 to the further milk analyzing unit 35 via the outlet conduit 122 in a flow direction F.

The liquid inlet port 113 is via a liquid conduit 123 connected to a liquid source 133 and permits liquid, preferably water, to be delivered to the flow channel 110. A liquid valve 143 is provided to open and close the liquid inlet port 113.

The gas inlet port 114 is via a gas conduit 124 connected to a gas source 134 and permits gas, preferably pressurized gas or pressurized air, to be delivered to the flow channel 110. A gas valve 144 is provided to open and close the gas inlet port 114. The gas inlet port 114 is located upstream the liquid inlet port 143 in relation to the flow direction F.

Each of the milk samples to be delivered to the further milk analyzing unit 35 has a determined volume being sufficient for permitting the further milk analyzing unit 35 to perform a milk analysis on the milk sample. The second distribution portion 9 provides a milk storing volume that is greater than said determined volume of each milk sample. Preferably, the milk storing volume of the second distribution portion 9 may be at least twice said determined volume of each milk sample, or at least three times greater than said determined volume, at least four times greater than said determined volume or at least five times greater than said determined volume of each milk sample.

According to the embodiment disclosed, the outlet conduit 122 provides the milk storing volume. Thus, the outlet conduit 122 has an internal volume that is greater than said determined volume, at least twice or at least three, four or five times said determined volume of each milk sample.

According the embodiment disclosed, the further milk analyzing unit 35 may thus be located at a remote position at a distance from the second distribution portion 9. The further milk analyzing unit 35 may for instance be located at a central control space (not disclosed) that is common for a plurality of milk stations.

Figure 14:
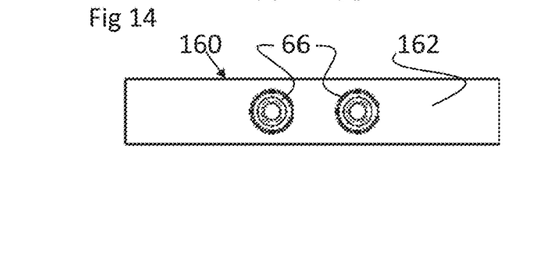
FIG. 14 shows bottom view of a membrane of a second distribution portion of the distribution unit.

Also the second distribution portion 9 comprises a membrane 160, see FIG. 14, having an elongated shape and extending in the flow channel 110 in parallel with the longitudinal axis x. The membrane 160 has a first side 161 facing the ports 111-114 and a second side 162 being opposite to the first side 161. The membrane 160 may be made of a rubber-like material.

The second distribution portion 9 comprises an upper part 163 supported by and attached to the lower part 64. The ports 111-114 extends through the upper part 163 as can be seen in FIG. 4. As can be seen in FIGS. 2-4, the upper part 63 of the first distribution portion 8 is separated from the upper part 163 of the second distribution portion 9.

The first side 161 of the membrane 160 is smooth and turned towards the flow channel 110 and the upper part 163 of the second distribution portion 9. The flow channel 110 is thus defined by the upper part 163 and the first side 161 of the membrane 160.

Each of the liquid inlet port 113 and the gas inlet port 114 is associated with and provided adjacent to a seat surface 153 and 154, see FIG. 4.

Each of the liquid inlet valve 143 and the gas inlet valve 144 comprises a valve body 65 acting on the second side 162 of the membrane 160 for closing and opening the respective ports 113 and 114.

Each of the valve bodies 65 is attached to the second side 162 of the membrane 160 to permit the valve body 65 to push the membrane 160 against the respective seat surface 152 and 153 for closing the respective port 113 and 114, and to pull the membrane 160 away from the respective seat surface 152 and 153 for opening the respective port 113 and 114.

As can be seen in FIG. 14, the membrane 160 comprises two engagement elements 66 protruding from the second side 162 of the membrane 160. Each of the valve bodies 65 of the valves 143, 144 is attached to the second side 162 of the membrane 160 via a respective one of the engagement elements 66, see FIG. 4.

The engagement element 66 of the membrane 160 have the same configuration as the engagement elements 66 and the membrane 60 of the first distribution portion 8 and are attached to the valve bodies 65 in the same way as the engagement elements 66 of the membrane 60. The above description with respect to FIGS. 7-13 thus applies also to the membrane 160 and the second distribution portion 9. The valves 143, 144 have the same configuration as the valves 43-45 and 47-49.

The further milk analyzing units 35 may include means for analyzing milk samples, in particular for making more complicated and time consuming analyzes of more advanced milk parameters, such a progesterone, LDH—Lactate Dehydrogenase, Urea, BHB—Beta Hydroxy Butyrate, etc. The analysis of these more advanced milk parameters is more time consuming than the analysis of the traditional milk parameters such as fat, protein and lactose contents. The further milk analyzing unit 35 may comprise a so called Herd Navigator™.

The control unit 90 is configured for controlling also the operation of the second distribution portion 9, in particular for controlling also the liquid inlet valve 143 and the gas inlet valve 144. Thus, the control unit 90 is configured to permit liquid to be delivered from the liquid source 133 to the flow channel 110 of the second distribution portion 9 by opening the liquid inlet valve 143. In the same way, the control unit 90 is configured to permit pressurized gas to be delivered from the gas source 134 to the flow channel 110 of the second distribution portion 9 by opening the gas inlet valve 144.

Operation

The milk sampling device 5 and the distribution unit 6 may be operated as follows. Initially, all valves 41-45, 47-49 are in a closed position. The control unit 90 initiates a rinsing process of the flow surfaces of the distribution unit 6 and the milk sampling pump 50. The control unit 90 opens the main valve 7 and opens the inlet valve 41. The flow channel 10 is then open and flow communication is created between the inlet conduit 21 and the entire flow channel 10.

The control unit 90 activates the actuator 50D of the milk sampling pump 50 to move the piston 50C from an initial position in which the first chamber 50A has a minimal size. The movement of the piston 50C expands the first chamber 50A and a low pressure is created in the first chamber 50A, the first pump conduit 26, the flow channel 10 and the inlet conduit 21.

When the piston 50C has reached a determined position and the first chamber 50A has received a determined quantity of milk, the control unit 90 closes the inlet valve 41. The milk flow from the inlet conduit 21 to the flow channel 10 ceases. The control unit 90 activates the actuator 50D to move the piston 50C in an opposite direction back towards the initial position. This movement of the piston 50C provides a milk flow from the first chamber 50A, via the first pump conduit 26 and the first pump 16, to the flow channel 10. All valves 41-45, 47-49 are closed and the pressure increases in the flow channel 10. The control unit 90 opens the drain valve 48 and the milk leaves the flow channel 10 via the drain conduit 28 to the drain outlet 38. This initial milk flow to the first distribution portion 8 cleans the inner surfaces of the first distribution portion 8 from milk residues of the previous milk sample. When the piston 50C has reached the initial position, the first chamber 50A of the milk sampling pump 50 has been emptied of rinsing milk.

Then the milk sampling process proper is initiated. The control unit 90 again opens the inlet valve 41. The control unit 90 activates the actuator 50D to move the piston 50C from the initial position. The first chamber 50A expands and a low pressure is created in the first pump conduit 26, the flow channel 10 and the inlet conduit 21 which creates a milk flow from the milk receiver 1 to the first chamber 50A via the inlet conduit 21, the flow channel 10 and the first pump conduit 26.

When the first chamber 50A has received a determined quantity of milk, the control unit 90 closes the inlet valve 41. The determined quantity of milk, now contained in the first chamber 50A, or a part of the determined quantity of milk, may then be delivered to any one of the first milk analysing units 32-35, for instance the first milk analysing unit 32. In this case, the control unit 90 opens the first outlet valve 42. The control unit 90 activates the actuator 50D to move the piston 50C in the direction towards the initial position. The piston 50C creates a milk flow from the first chamber 50A, via the first pump conduit 26, the first pump port 16, the flow channel 10, the milk outlet port 12, the first outlet conduit 22, to the first milk analyzing unit 32.

It should be noted that the determined quantity of milk contained in first chamber 50A could be supplied to more than one of the milk outlet conduits 22-25 and thus be distributed to several of the milk analysing units 32-35.

In a corresponding manner, milk may be supplied to the flow channel 110 of the second distribution portion 9 via the outlet port 15, the fourth outlet valve 45 and the fourth outlet conduit 25.

When milk has been received in the flow channel 110 of the second distribution unit 9, the control unit 90 closes the outlet valve 45 and opens the liquid inlet valve 143 in order to permit a volume of liquid to be introduced into the flow channel 110 of the second distribution portion 9 and to be located, seen in the flow direction F, behind a determined volume of milk contained in the flow channel 110 and the outlet conduit 122. The volume of liquid may thus create a limit of said determined volume of milk to permit said determined volume of milk to be separated from the following milk sample.

The control unit 90 may then close the liquid inlet valve 143 after said volume of liquid has been delivered from the liquid source 133 and open the gas inlet valve 144 to permit pressurized gas to be introduced into the flow channel 110 of the second distribution portion 9 from the gas source 134 in order to push said volume of liquid and said determined volume of milk in the flow direction F in the outlet conduit 122 towards the further milk analyzing unit 35.

One or more of said determined volumes of milk may then be introduced and transported into the outlet conduit 122, wherein each volume is separated from adjacent volumes by a volume of liquid introduced from the liquid source 133 via the liquid inlet conduit 123.

The distribution unit 6 and the conduits 21-25, 28, 29 may be washed at regular intervals. When a washing process is to be performed, the control unit 90 opens the inlet valve 41 to permit introduction of a washing liquid from a washing liquid source (not disclosed) via the inlet conduit 21. Then, the control unit 90 may open one or several of the valves 42-45, 48, 49 in order to provide a washing liquid flow through one or several of the ports 12-17 and the conduits 22-29. The washing liquid flow ceases when the control unit 90 closes the inlet valve 41. In a corresponding manner, it is possible to supply and wash the pump conduits 26, 27 and the chambers 50A and 50B and the piston 50C of the pump 50 with washing liquid.

The invention is not restricted to the described embodiment but may be varied and modified within the scope of the following claims.

The invention claimed is:

1. A milk sampling device (5) comprising at least two milk analyzing units (32-34), a further milk analyzing unit (35), and a distribution unit (6) for milk samples, comprising:
   a first distribution portion (8) that includes a first flow channel (10) and a first plurality of ports which adjoin and communicate with the first flow channel (10),
   the first plurality of ports comprising at least
      a first milk inlet port (11) that permits milk to be delivered to the first flow channel, and
      at least two first milk outlet ports (12-15) connected to the at least two milk analyzing units (32-34) and that permit first milk samples to be delivered from the first flow channel (10) to the respective at least two milk analyzing units (32-34); and a second distribution portion (9) that includes a second flow channel (110) and a second plurality of ports which adjoin and communicate with the second flow channel (110) of the second distribution portion (9), wherein the second flow channel (110) of the second distribution portion (9) is separated from the first flow channel (10) of the first distribution portion (8), and wherein the second plurality of ports comprises at least a second milk inlet port (111) that permits milk to be delivered from the first flow channel (10) of the first distribution portion (8) to the second flow channel (110) of the second distribution portion (9), and a milk outlet port (112) connected to the further milk analyzing unit (35) and that permits second milk samples to be delivered from the second flow channel (110) of the second distribution portion (9) in a flow direction (F) to the further milk analyzing unit (35), and wherein the second plurality of ports of the second distribution portion (9) also comprises a liquid inlet port (113), connected to a liquid source (133) via a liquid inlet valve (143), and a gas inlet port (114), connected to a gas source (134) via a gas inlet valve (144).

2. The milk sampling device (5) comprising the at least two milk analyzing units (32-34), the further milk analyzing unit (35), and the distribution unit (6) according to claim 1, wherein each of the second milk samples to be delivered to the further milk analyzing unit (35) has a determined volume for the further milk analyzing unit (35) to perform a milk analysis, and wherein the second distribution portion (9) provides a milk storing volume that is greater than said determined volume.

3. The milk sampling device (5) comprising the at least two milk analyzing units (32-34), the further milk analyzing unit (35), and the distribution unit (6) according to claim 2, wherein the milk storing volume of the second distribution portion (9) is at least twice said determined volume.

4. The milk sampling device (5) comprising the at least two milk analyzing units (32-34), the further milk analyzing unit (35), and the distribution unit (6) according to claim 2, further comprising:

an outlet conduit (122) connecting the milk outlet port (112) to the further milk analyzing unit (35), wherein the milk storing volume is provided by an internal volume of the outlet conduit (122), said internal volume being greater than said determined volume.

5. The milk sampling device (5) comprising the at least two milk analyzing units (32-34), the further milk analyzing unit (35), and the distribution unit (6) according to claim 4, wherein the further milk analyzing unit (35) is located at a remote position at a distance from the distribution unit (6).

6. The milk sampling device (5) comprising the at least two milk analyzing units (32-34), the further milk analyzing unit (35), and the distribution unit (6) according to claim 1, further comprising:

a control unit (90) configured to permit liquid to be delivered from the liquid source (133) to the second flow channel (110) of the second distribution portion (9) by opening the liquid inlet valve (143).

7. The milk sampling device (5) comprising the at least two milk analyzing units (32-34), the further milk analyzing unit (35), and the distribution unit (6) according to claim 6, wherein the control unit (90) is configured to open the liquid inlet valve (143) after a volume of milk for analysis by the further milk analyzing unit (35) has been delivered from the first flow channel (10) of the first distribution portion (8) to permit a volume of liquid to be introduced into the second flow channel (110) of the second distribution portion (9) and located behind said volume of milk in the flow direction (F).

8. The milk sampling device (5) comprising the at least two milk analyzing units (32-34), the further milk analyzing unit (35), and the distribution unit (6) according to claim 6, wherein the control unit (90) is further configured to permit pressurized gas to be delivered from the gas source (134) to the second flow channel (110) of the second distribution portion (9) by opening the gas inlet valve (144).

9. The milk sampling device (5) comprising the at least two milk analyzing units (32-34), the further milk analyzing unit (35), and the distribution unit (6) according to claim 7, wherein the control unit (90) is further configured to open the gas inlet valve (144) after said volume of liquid has been delivered from the liquid source (133) to permit pressurized gas to be introduced into the second flow channel (110) of the second distribution portion (9) in order to push said volume of liquid and said volume of milk in the flow direction towards the further milk analyzing unit (35).

10. The milk sampling device (5) comprising the at least two milk analyzing units (32-34), the further milk analyzing unit (35), and the distribution unit (6) according to claim 1, wherein the first distribution portion (8) comprises a first upper part (63), through which the first plurality of ports of the first distribution portion (8) extend, and the second distribution portion (9) comprises a second upper part (163), through which the second plurality of ports of the second distribution portion (9) extend, and wherein the first upper part (63) of the first distribution portion (8) is separated from the second upper part (163) of the second distribution portion (9).

11. The milk sampling device (5) comprising the at least two milk analyzing units (32-34), the further milk analyzing unit (35), and the distribution unit (6) according to claim 1, wherein the first flow channel (10) of the first distribution portion (8) and the second flow channel (110) of the second distribution portion (9) extend in parallel with a common longitudinal axis (x).

* * * * *